United States Patent
Arlen et al.

(10) Patent No.: US 12,037,410 B2
(45) Date of Patent: Jul. 16, 2024

(54) METHODS AND COMPOSITIONS FOR TARGETING TREG CELLS

(71) Applicant: PRECISION BIOLOGICS, INC., Bethesda, MD (US)

(72) Inventors: Philip M. Arlen, Bethesda, MD (US); Kwong Y. Tsang, Bethesda, MD (US); Justin M. David, Bethesda, MD (US); Massimo Fantini, Bethesda, MD (US)

(73) Assignee: PRECISION BIOLOGICS, INC., Bethesda, MD (US)

( * ) Notice: Subject to any disclaimer, the term of this patent is extended or adjusted under 35 U.S.C. 154(b) by 843 days.

(21) Appl. No.: 16/969,268

(22) PCT Filed: Feb. 13, 2019

(86) PCT No.: PCT/US2019/017870
§ 371 (c)(1),
(2) Date: Aug. 12, 2020

(87) PCT Pub. No.: WO2019/160970
PCT Pub. Date: Aug. 22, 2019

(65) Prior Publication Data
US 2021/0002383 A1    Jan. 7, 2021

Related U.S. Application Data

(60) Provisional application No. 62/630,084, filed on Feb. 13, 2018.

(51) Int. Cl.
*C07K 16/30* (2006.01)
*A61K 39/395* (2006.01)
*A61K 39/00* (2006.01)
*A61K 45/06* (2006.01)

(52) U.S. Cl.
CPC ............ *C07K 16/30* (2013.01); *A61K 39/395* (2013.01); *A61K 2039/505* (2013.01); *A61K 45/06* (2013.01); *C07K 2317/24* (2013.01); *C07K 2317/732* (2013.01); *C07K 2317/734* (2013.01)

(58) Field of Classification Search
CPC ............... C07K 16/30; C07K 2317/24; C07K 2317/32; C07K 2317/34; A61K 39/395; A61K 2039/505
See application file for complete search history.

(56) References Cited

U.S. PATENT DOCUMENTS

| | | | |
|---|---|---|---|
| 7,314,622 B2 | 1/2008 | Arlen et al. | |
| 7,763,720 B2 | 7/2010 | Arlen et al. | |
| 7,829,678 B2 | 11/2010 | Bristol et al. | |
| 8,470,326 B2 | 6/2013 | Bristol et al. | |
| 8,524,456 B2 | 9/2013 | Bristol et al. | |
| 8,535,667 B2 | 9/2013 | Arlen et al. | |
| 8,802,090 B2 * | 8/2014 | Bristol | G01N 33/57419 424/130.1 |
| 9,034,588 B2 | 5/2015 | Bristol et al. | |
| 9,068,014 B2 | 6/2015 | Wang | |
| 9,169,326 B2 | 10/2015 | Arlen et al. | |
| 9,371,375 B2 | 6/2016 | Bristol et al. | |
| 9,592,290 B2 | 3/2017 | Bristol et al. | |
| 9,605,077 B2 | 3/2017 | Arlen et al. | |
| 9,718,866 B2 | 8/2017 | Wang | |
| 9,938,344 B2 | 4/2018 | Wang et al. | |
| 10,023,650 B2 | 7/2018 | Bristol et al. | |
| 10,364,295 B2 | 7/2019 | Arlen et al. | |
| 10,533,040 B2 | 1/2020 | Wang | |
| 10,689,443 B2 | 6/2020 | Wang et al. | |
| 11,001,641 B2 | 5/2021 | Bristol et al. | |
| 11,279,768 B1 * | 3/2022 | Arlen | C07K 16/3046 |
| 2013/0189268 A1 | 7/2013 | Du et al. | |
| 2015/0376276 A1 * | 12/2015 | Lewis | A61P 35/02 536/23.53 |
| 2019/0322720 A1 | 10/2019 | Du et al. | |
| 2019/0322759 A1 | 10/2019 | Arlen et al. | |
| 2020/0155662 A1 * | 5/2020 | Jones | A61K 39/0011 |
| 2020/0165310 A1 | 5/2020 | Wang | |
| 2020/0255535 A1 | 8/2020 | Bristol et al. | |
| 2020/0362053 A1 | 11/2020 | Arlen et al. | |
| 2021/0002368 A1 | 1/2021 | Wang et al. | |

FOREIGN PATENT DOCUMENTS

| | | |
|---|---|---|
| WO | 2010105298 | 9/2010 |
| WO | 2011163401 | 12/2011 |

OTHER PUBLICATIONS

Paul, Fundamental Immunology, 3rd Edition, 1993, pp. 292-295.*
Colman, Research in Immunology, 1994, 145:33-36.*
Rudikoff et al., Proc. Natl. Acad. Sci. USA, 1982, 79(6):1979-1983.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al., Journal of Immunological Methods, vol. 463, p. 127-133, 2018.*
Fantini et al. "Preclinical characterization of a novel monoclonal antibody NEO-201 for the treatment of human carcinomas." Frontiers in immunology. Jan. 4, 2018;8:1899, pp. 1-14.
Kim et al. "A phase II therapeutic, open label, multi-center clinical trial of NPC-1C, a chimeric monoclonal antibody (mAb), in adults with chemotherapy refractory metastatic colorectal cancer (mCRC), initial results." (2016): p. 500.

(Continued)

*Primary Examiner* — Hong Sang
(74) *Attorney, Agent, or Firm* — Robin L. Teskin; Baker, Donelson, Bearman, Caldwell & Berkowitz PC

(57) ABSTRACT

The antibody NEO-201 is shown to bind to Treg cells, and its use in targeting Treg cells is described. NEO-201 may be used for isolation, detection, or purification of active Treg cells and also to kill Treg cells. Therapeutic methods and combination therapies using NEO-201 optionally in combination with another agent are described.

12 Claims, 3 Drawing Sheets

Specification includes a Sequence Listing.

(56) References Cited

OTHER PUBLICATIONS

Hendlisz et al. "Phase III trial comparing protracted intravenous fluorouracil infusion alone or with yttrium-90 resin microspheres radioembolization for liver-limited metastatic colorectal cancer refractory to standard chemotherapy." J Clin Oncol. Aug. 10, 2010;28(23):3687-94.
Monica K. Neuman, Lidia Hernandez, Xue-Ping Wang, Olga Saric, Alex Dubeykovskiy, Philip Arlen, Christina M. Annunziata; Abstract 1496: Identification of target and cytotoxicity of novel monoclonal antibody NEO-201 in ovarian and uterine cancer subtypes. Cancer Res Jul. 15, 2016; 76 (14_Supplement): 1496. https://doi.org/10.1158/1538-7445.AM2016-1496.
Kristen Zeligs, Philip M. Arlen, Kwong Tsang, Lidia Hernandez, Massimo Fantini, Christina M. Annunziata; Abstract 3025: Preclinical characterization of a novel monoclonal antibody targeting a neo-antigen expressed in ovarian and GI malignancies. Cancer Res Jul. 1, 2017; 77 (13_Supplement): 3025. https://doi.org/10.1158/1538-7445.AM2017-3025.
Arlen et al., "The Discovery and Development of Novel Monoclonal Antibodies Targeting Neoantigens", precision biologics, URL:https://precision-biologics.com/wp-content/uploads/PB-GTC-BIO-san-diego-feb-2017-Arlen.pdf, Feb. 1, 2017 (Feb. 1, 2017).

\* cited by examiner

FIG. 1. Percentage of functional Tregs isolated using commercial kit[1] or based on NEO-201 expression[2]

| [1]EasySep™ Human CD4+CD127lowCD25+ Regulatory T Cell Isolation kit | [2]EasySep™ Release Human Biotin NEO-201 Positive Selection Kit |
|---|---|
| 67.14* | 99.12# |

Results are expressed in average % of NEO-201+/CD15s+ cells in CD4+/CD25high/FOXp3+ cells (N = 3*)
from one donor.

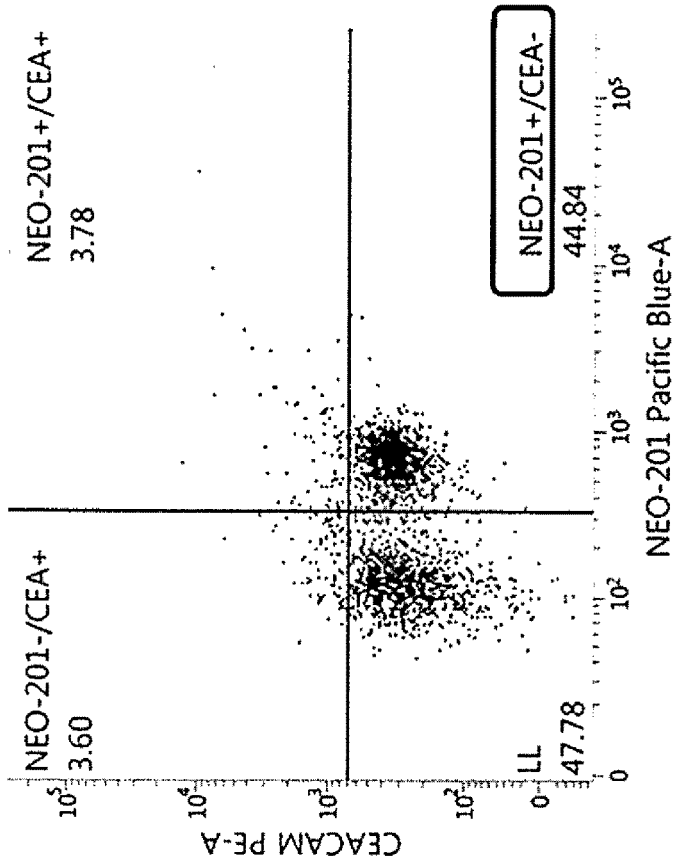

FIG. 2. Regulatory T-cells are CEACAM-5 and CEACAM-6 negative as determined by flow cytometry. Phenotypic analysis of isolated T-regs (EasySep™ Human CD4+CD127lowCD25+ Regulatory T Cell Isolation kit (HD 19).

44.84% of CD4+/CD25high/CD127-/FOXp3+ cells are NEO-201+/CEACAM5- and CEACAM6- cells Cells were stained with PE Mouse Anti-Human CD66 antibody ( Clone B1.1/CD66) which recognizes CD66a (*CEACAM1*), CD66c (*CEACAM6*), CD66d (*CEACAM3*) and CD66e (*CEACAM5*)

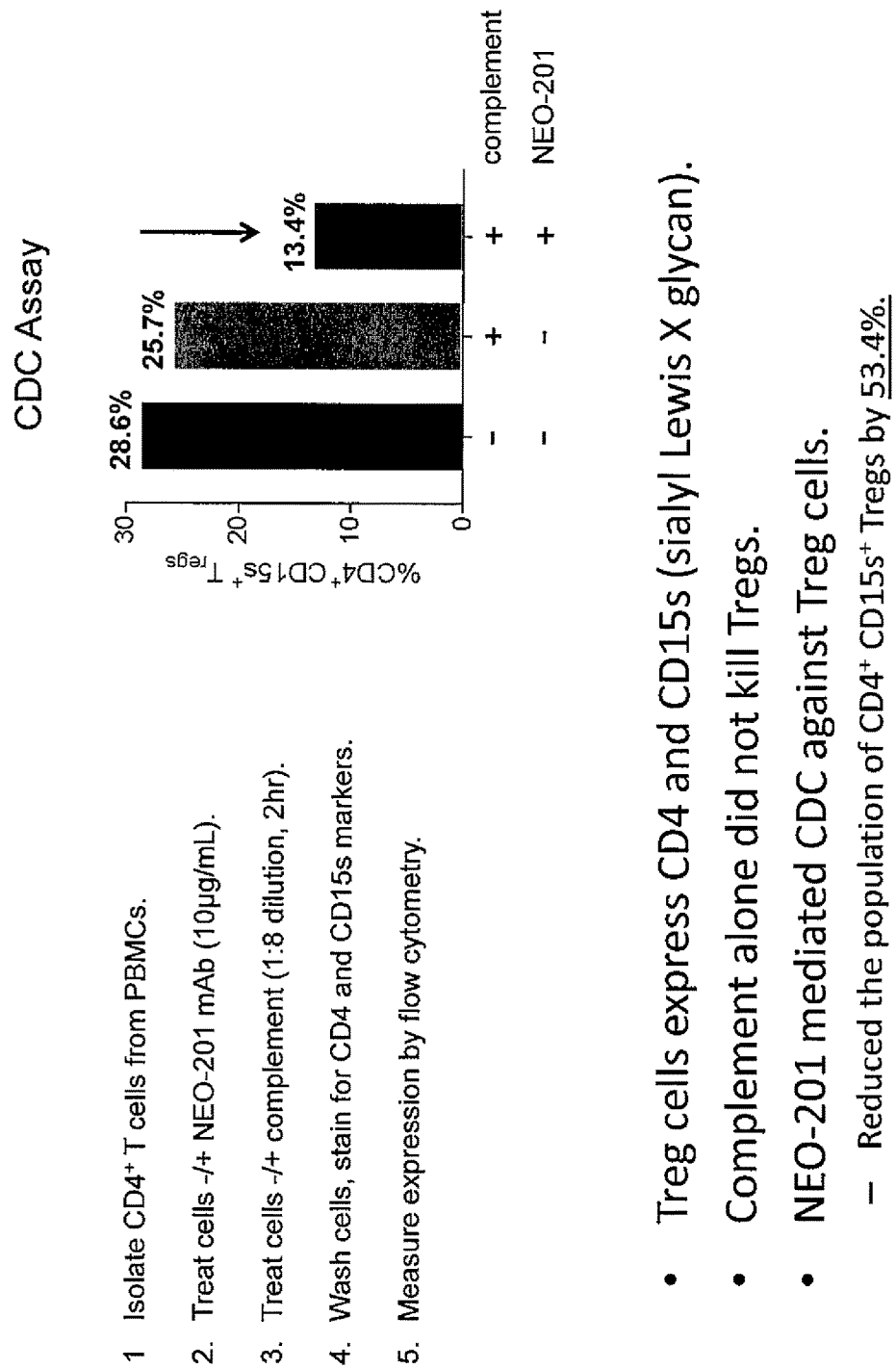

SEQUENCE LISTING

```
<160> NUMBER OF SEQ ID NOS: 39

<210> SEQ ID NO 1
<211> LENGTH: 11
<212> TYPE: PRT
<213> ORGANISM: Mus musculus

<400> SEQUENCE: 1

Gly Ala Ser Glu Asn Ile Tyr Gly Ala Leu Asn
1               5                   10

<210> SEQ ID NO 2
<211> LENGTH: 7
<212> TYPE: PRT
<213> ORGANISM: Mus musculus

<400> SEQUENCE: 2

Gly Ala Ser Asn Leu Ala Asp
1               5

<210> SEQ ID NO 3
<211> LENGTH: 9
<212> TYPE: PRT
<213> ORGANISM: Mus musculus

<400> SEQUENCE: 3

Gln Asn Val Leu Ser Ser Pro Tyr Thr
1               5

<210> SEQ ID NO 4
<211> LENGTH: 11
<212> TYPE: PRT
<213> ORGANISM: Homo sapiens
```

<400> SEQUENCE: 4

Gln Ala Ser Glu Asn Ile Tyr Gly Ala Leu Asn
1               5                   10

<210> SEQ ID NO 5
<211> LENGTH: 7
<212> TYPE: PRT
<213> ORGANISM: Homo sapiens

<400> SEQUENCE: 5

Gly Ala Ser Asn Leu Ala Thr
1               5

<210> SEQ ID NO 6
<211> LENGTH: 9
<212> TYPE: PRT
<213> ORGANISM: Homo sapiens

<400> SEQUENCE: 6

Gln Gln Val Leu Ser Ser Pro Tyr Thr
1               5

<210> SEQ ID NO 7
<211> LENGTH: 10
<212> TYPE: PRT
<213> ORGANISM: Mus musculus

<400> SEQUENCE: 7

Gly Tyr Thr Phe Thr Asp Tyr Ala Met His
1               5                   10

<210> SEQ ID NO 8
<211> LENGTH: 17
<212> TYPE: PRT
<213> ORGANISM: Mus musculus

<400> SEQUENCE: 8

Leu Ile Ser Thr Tyr Ser Gly Asp Thr Lys Tyr Asn Gln Asn Phe Lys
1               5                   10                  15

Gly

<210> SEQ ID NO 9
<211> LENGTH: 12
<212> TYPE: PRT
<213> ORGANISM: Mus musculus

<400> SEQUENCE: 9

Gly Asp Tyr Ser Gly Ser Arg Tyr Trp Phe Ala Tyr
1               5                   10

<210> SEQ ID NO 10
<211> LENGTH: 17
<212> TYPE: PRT
<213> ORGANISM: Homo sapiens

<400> SEQUENCE: 10

Leu Ile Ser Thr Tyr Ser Gly Asp Thr Lys Tyr Asn Gln Asn Phe Gln
1               5                   10                  15

Gly

<210> SEQ ID NO 11
<211> LENGTH: 12
<212> TYPE: PRT

<213> ORGANISM: Homo sapiens

<400> SEQUENCE: 11

Gly Asp Tyr Ser Gly Ser Arg Tyr Trp Phe Ala Tyr
1               5                   10

<210> SEQ ID NO 12
<211> LENGTH: 965
<212> TYPE: DNA
<213> ORGANISM: Mus musculus

<400> SEQUENCE: 12

```
gcggggcagc ctcacacaga acacacacag atatgggtgt acccactcag ctcctgttgc      60
tgtggcttac agtcgtagtt gtcagatgtg acatccagat gactcagtct ccagcttcac     120
tgtctgcatc tgtgggagaa actgtcacca tcacatgtgg agcaagtgag aatatttacg     180
gtgctttaaa ttggtatcag cggaaacagg gaaaatctcc tcagctcctg atttatggcg     240
caagtaattt ggcagatggc atgtcatcga ggttcagtgg cagtggatct ggtagacagt     300
attctctcaa gatcagtagc ctgcatcctg acgatgttgc aacgtattac tgtcaaaatg     360
tattaagtag tccgtacacg ttcggagggg gaccaagctg gaaataaaaa cgggctgatg     420
ctgcaccaac tgtatccatc ttcccaccat ccagtgagca gttaacatct ggaggtgcct     480
cagtcgtgtg cttcttgaac aacttctacc ccaaagacat caatgtcaag tggaagattg     540
atggcagtga acgacaaaat ggcgtcctga acagttggac tgatcaggac agcaaagaca     600
gcacctacag catgagcagc accctcacgt tgaccaagga cgagtatgaa cgacataaca     660
gctatacctg tgaggccact cacaagacac caacttcacc cattgtcaag agcttcaaca     720
ggaatgagtg ttagagacaa aggtcctgag acgccaccac cagctcccca gctccatcct     780
atcttcccct ctaaggtctt ggaggcttcc ccacaagcga cctaccactg ttgcggtgct     840
ccaaacctcc tccccacctc cttcctctcc tcctcccttt ccttggcttt tatcatgcta     900
atatttgcag aaaatattca ataaagtgag tctttgcaca aaaaaaaaa aaaaaaaaa      960
aaaaa                                                                 965
```

<210> SEQ ID NO 13
<211> LENGTH: 1575
<212> TYPE: DNA
<213> ORGANISM: Mus musculus

<400> SEQUENCE: 13

```
acgcgggaca cagtagtctc tacagtcaca ggagtacaca ggacattgcc atgggttgga      60
gctgtatcat cttctttctg gtagcaacag ctacaggtgt gcactccccag gtccagctgc     120
agcagtctgg gcctgaggtg gtgaggcctg ggtctcagt gaagatttcc tgcaaggggtt     180
ccggctacac attcactgat tatgctatgc actgggtgaa gcagagtcat gcaaagagtc     240
tcgagtggat tggacttatt agtacttaca gtggtgatac aaagtacaac cagaacttta     300
agggcaaggc cacaatgact gtagacaaat cctccaacac agcctatatg gaacttgcca     360
gattgacatc tgaggattct gccatctatt actgtgcaag aggggattat tccggtagta     420
ggtactggtt tgcttactgg ggccaaggga ctctggtcac tgtctctgca gccaaaacga     480
cacccccatc tgtctatcca ctggcccctg gatctgctgc ccaaactaac tccatggtga     540
ccctgggatg cctggtcaag ggctatttcc ctgagccagt gacagtgacc tggaactctg     600
gatccctgtc cagcggtgtg cacaccttcc cagctgtcct gcagtctgac ctctacactc     660
```

```
tgagcagctc agtgactgtc ccctccagca cctggcccag cgagaccgtc acctgcaacg    720
ttgcccaccc ggccagcagc accaaggtgg acaagaaaat tgtgcccagg gattgtggtt    780
gtaagccttg catatgtaca gtcccagaag tatcatctgt cttcatcttc ccccaaagc    840 ccaaggatgt gctcaccatt actctgactc ctaaggtcac gtgtgttgtg gtagacatca    900
gcaaggatga tcccgaggtc cagttcagct ggtttgtaga tgatgtggag gtgcacacag    960
ctcagacgca accccgggag gagcagttca cagcactttt ccgctcagtc agtgaacttc   1020
ccatcatgca ccaggactgg ctcaatggca aggagttcaa atgcagggtc aacagtgcag   1080
ctttccctgc ccccatcgag aaaccatctc caaaaccaa aggcagaccg aaggctccac   1140
aggtgtacac cattccacct cccaaggagc agatggccaa ggataaagtc agtctgacct   1200
gcatgataac agacttcttc cctgaagaca ttactgtgga gtggcagtgg aatgggcagc   1260
cagcggagaa ctacaagaac actcagccca tcatggacac agatggctct tacttcgtct   1320
acagcaagct caatgtgcag aagagcaact gggaggcagg aaatactttc acctgctctg   1380
tgttacatga gggcctgcac aaccaccata ctgagaagag cctctcccac tctcctggta   1440
aatgatccca gtgtccttgg agccctctgg ccctacagga ctttgacacc tacctccacc   1500
cctccctgta taaataaagc acccagcact gcctcgggac cctgcataaa aaaaaaaaa   1560 aaaaaaaaaa aaaaa                                                     1575

<210> SEQ ID NO 14
<211> LENGTH: 107
<212> TYPE: PRT
<213> ORGANISM: Mus musculus

<400> SEQUENCE: 14

Leu Met Thr Gln Ser Pro Ala Ser Leu Ser Ala Ser Val Gly Glu Thr
1               5                  10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Ser Pro Tyr Thr Phe
                85                  90                  95

Gly Gly Gly Thr Lys Leu Glu Ile Lys Lys Gly
            100                 105

<210> SEQ ID NO 15
<211> LENGTH: 116
<212> TYPE: PRT
<213> ORGANISM: Mus musculus

<400> SEQUENCE: 15

Leu Glu Glu Ser Gly Pro Glu Val Val Arg Pro Gly Val Ser Val Lys
1               5                  10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
```

```
                    50                  55                  60

Ala Thr Met Thr Val Asp Lys Ser Ser Asn Thr Ala Tyr Met Glu Leu
 65                  70                  75                  80

Ala Arg Leu Thr Ser Glu Asp Ser Ala Ile Tyr Tyr Cys Ala Arg Gly
                     85                  90                  95

Asp Tyr Ser Gly Ser Arg Tyr Trp Phe Ala Tyr Trp Gly Gln Gly Thr
                100                 105                 110

Thr Val Thr Arg
            115

<210> SEQ ID NO 16
<211> LENGTH: 107
<212> TYPE: PRT
<213> ORGANISM: Mus musculus

<400> SEQUENCE: 16

Asp Ile Gln Met Thr Gln Ser Pro Ala Ser Leu Ser Ala Ser Val Gly
 1               5                  10                  15

Glu Thr Val Thr Ile Thr Cys Gly Ala Ser Glu Asn Ile Tyr Gly Ala
                 20                  25                  30

Leu Asn Trp Tyr Gln Arg Lys Gln Gly Lys Ser Pro Gln Leu Leu Ile
             35                  40                  45

Tyr Gly Ala Ser Asn Leu Ala Asp Gly Met Ser Ser Arg Phe Ser Gly
         50                  55                  60

Ser Gly Ser Gly Arg Gln Tyr Ser Leu Lys Ile Ser Ser Leu His Pro
 65                  70                  75                  80

Asp Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 17

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Arg Lys Pro Gly Lys Ser Pro Lys Leu Leu Ile
             35                  40                  45

Tyr Gly Ala Ser Asn Leu Ala Asp Gly Met Pro Ser Arg Phe Ser Gly
         50                  55                  60

Ser Gly Ser Gly Arg Gln Tyr Thr Leu Thr Ile Ser Ser Leu Gln Pro
 65                  70                  75                  80

Glu Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
            100                 105

<210> SEQ ID NO 18
<211> LENGTH: 107
<212> TYPE: PRT
<213> ORGANISM: Artificial Sequence
```

<220> FEATURE:
<223> OTHER INFORMATION: Humanized antibody sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial sequence
<220> FEATURE:
<223> OTHER INFORMATION: Humanized antibody sequence

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: Artificial sequence
<220> FEATURE:
<223> OTHER INFORMATION: Humanized antibody sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

```
Ser Gly Ser Gly Arg Gln Tyr Thr Phe Thr Ile Ser Ser Leu Gln Pro
 65                  70                  75                  80

Glu Asp Ile Ala Thr Tyr Tyr Cys Gln Gln Val Leu Ser Ser Pro Tyr
                 85                  90                  95

Thr Phe Gly Gly Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Humanized antibody sequence

<400> SEQUENCE: 21

```
Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                20                  25                  30

Leu Asn Trp Tyr Gln Arg Lys Pro Gly Lys Ser Pro Asn Leu Leu Ile
             35                  40                  45

Tyr Gly Ala Ser Asn Leu Ala Asp Gly Met Pro Ser Arg Phe Ser Gly
 50                  55                  60

Ser Gly Ser Gly Arg Gln Tyr Thr Leu Thr Ile Ser Ser Leu Gln Pro
 65                  70                  75                  80

Glu Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
            100                 105
```

<210> SEQ ID NO 22
<211> LENGTH: 121
<212> TYPE: PRT
<213> ORGANISM: Mus musculus

<400> SEQUENCE: 22

```
Gln Val Gln Leu Gln Gln Ser Gly Pro Glu Val Val Arg Pro Gly Val
 1               5                  10                  15

Ser Val Lys Ile Ser Cys Lys Gly Ser Gly Tyr Thr Phe Thr Asp Tyr
                20                  25                  30

Ala Met His Trp Val Lys Gln Ser His Ala Lys Ser Leu Glu Trp Ile
             35                  40                  45

Gly Leu Ile Ser Thr Tyr Ser Gly Asp Thr Lys Tyr Asn Gln Asn Phe
 50                  55                  60

Lys Gly Lys Ala Thr Met Thr Val Asp Lys Ser Ser Asn Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ala
        115                 120
```

<210> SEQ ID NO 23
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 23

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
            115                 120
```

<210> SEQ ID NO 24
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
            115                 120
```

<210> SEQ ID NO 25
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Met
        35                  40                  45
```

```
Gly Leu Ile Ser Thr Tyr Ser Gly Asp Thr Lys Tyr Ser Gln Lys Phe
        50                  55                  60

Gln Gly Arg Val Thr Met Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
            115                 120

<210> SEQ ID NO 26
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 26

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Ala Met His Trp Val Arg Gln Ala Pro Gly Gln Arg Leu Glu Trp Ile
             35                  40                  45

Gly Leu Ile Ser Thr Tyr Ser Gly Asp Thr Lys Tyr Asn Gln Lys Phe
        50                  55                  60

Gln Gly Lys Ala Thr Met Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
            115                 120

<210> SEQ ID NO 27
<211> LENGTH: 121
<212> TYPE: PRT
<213> ORGANISM: Artificial sequence
<220> FEATURE:
<223> OTHER INFORMATION: Humanized antibody sequence

<400> SEQUENCE: 27

Gln Val Gln Leu Val Gln Ser Gly Ala Glu Val Lys Lys Pro Gly Ala
 1               5                  10                  15

Ser Val Lys Val Ser Cys Lys Gly Ser Gly Tyr Thr Phe Thr Asp Tyr
                 20                  25                  30

Ala Met His Trp Val Arg Gln Val His Ala Gln Gly Leu Glu Trp Ile
             35                  40                  45

Gly Leu Ile Ser Thr Tyr Ser Gly Asp Thr Lys Tyr Asn Gln Asn Phe
        50                  55                  60

Lys Gly Lys Ala Thr Met Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Tyr Ser Gly Ser Arg Tyr Trp Phe Ala Tyr Trp Gly
```

```
              100                 105                 110
Gln Gly Thr Leu Val Thr Val Ser Ser
            115                 120

<210> SEQ ID NO 28
<211> LENGTH: 470
<212> TYPE: PRT
<213> ORGANISM: Artificial sequence
<220> FEATURE:
<223> OTHER INFORMATION: Humanized antibody sequence (h16C3-Abb* heavy
      chain)
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(140)
<223> OTHER INFORMATION: Variable region
<220> FEATURE:
<221> NAME/KEY: MISC_FEATURE
<222> LOCATION: (141)..(470)
<223> OTHER INFORMATION: Constant region
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (70)..(85)
<223> OTHER INFORMATION: CDR2
<220> FEATURE:
<221> NAME/KEY: MISC_FEATURE
<222> LOCATION: (118)..(129)
<223> OTHER INFORMATION: CDR3

<400> SEQUENCE: 28

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
    50                  55                  60

Glu Trp Met Gly Leu Ile Ser Thr Tyr Ser Gly Asp Thr Lys Tyr Asn
65                  70                  75                  80

Gln Asn Phe Gln Gly Arg Val Thr Met Thr Val Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 29
<211> LENGTH: 233
<212> TYPE: PRT
<213> ORGANISM: Artificial sequence
<220> FEATURE:
<223> OTHER INFORMATION: Humanized antibody sequence (h16C3-Abb* light
      chain)
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(127)
<223> OTHER INFORMATION: Variable region
<220> FEATURE:
<221> NAME/KEY: MISC_FEATURE
<222> LOCATION: (128)..(233)
<223> OTHER INFORMATION: Constant region
<220> FEATURE:
<221> NAME/KEY: MISC_FEATURE
<222> LOCATION: (43)..(53)
<223> OTHER INFORMATION: CDR1
<220> FEATURE:
<221> NAME/KEY: MISC_FEATURE
<222> LOCATION: (69)..(75)
<223> OTHER INFORMATION: CDR2

```
<220> FEATURE:
<221> NAME/KEY: MISC_FEATURE
<222> LOCATION: (108)..(116)
<223> OTHER INFORMATION: CDR3

<400> SEQUENCE: 29

Met Gly Val Pro Thr Gln Leu Leu Leu Trp Leu Thr Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 30
<211> LENGTH: 17
<212> TYPE: PRT
<213> ORGANISM: Homo sapiens

<400> SEQUENCE: 30

Leu Ile Ser Thr Tyr Ser Gly Asp Thr Lys Tyr Ser Gln Lys Phe Gln
1               5                   10                  15

Gly

<210> SEQ ID NO 31
<211> LENGTH: 17
<212> TYPE: PRT
<213> ORGANISM: Artificial sequence
<220> FEATURE:
<223> OTHER INFORMATION: Humanized antibody sequence

<400> SEQUENCE: 31

Leu Ile Ser Thr Tyr Ser Gly Asp Thr Lys Tyr Asn Gln Lys Phe Gln
1               5                   10                  15

Gly
```

<210> SEQ ID NO 32
<211> LENGTH: 10
<212> TYPE: PRT
<213> ORGANISM: Artificial sequence
<220> FEATURE:
<223> OTHER INFORMATION: Humanized antibody sequence (h16C3-Abb* heavy chain CDR1)

<400> SEQUENCE: 32

Gly Tyr Thr Phe Thr Asp Tyr Ala Met His
1               5                   10

<210> SEQ ID NO 33
<211> LENGTH: 16
<212> TYPE: PRT
<213> ORGANISM: Artificial sequence
<220> FEATURE:
<223> OTHER INFORMATION: Humanized antibody sequence (h16C3-Abb* heavy chain CDR2)

<400> SEQUENCE: 33

Ile Ser Thr Tyr Ser Gly Asp Thr Lys Tyr Asn Gln Asn Phe Gln Gly
1               5                   10                  15

<210> SEQ ID NO 34
<211> LENGTH: 12
<212> TYPE: PRT
<213> ORGANISM: Artificial sequence
<220> FEATURE:
<223> OTHER INFORMATION: Humanized antibody sequence (h16C3-Abb* heavy chain CDR3)

<400> SEQUENCE: 34

Gly Asp Tyr Ser Gly Ser Arg Tyr Trp Phe Ala Tyr
1               5                   10

<210> SEQ ID NO 35
<211> LENGTH: 11
<212> TYPE: PRT
<213> ORGANISM: Artificial sequence
<220> FEATURE:
<223> OTHER INFORMATION: Humanized antibody sequence (h16C3-Abb* light chain CDR1)

<400> SEQUENCE: 35

Gln Ala Ser Glu Asn Ile Tyr Gly Ala Leu Asn
1               5                   10

<210> SEQ ID NO 36
<211> LENGTH: 7
<212> TYPE: PRT
<213> ORGANISM: Artificial sequence
<220> FEATURE:
<223> OTHER INFORMATION: Humanized antibody sequence (h16C3-Abb* light chain CDR2)

<400> SEQUENCE: 36

Gly Ala Ser Asn Leu Ala Thr
1               5

<210> SEQ ID NO 37
<211> LENGTH: 9
<212> TYPE: PRT
<213> ORGANISM: Artificial sequence
<220> FEATURE:
<223> OTHER INFORMATION: Humanized antibody sequence (h16C3-Abb* light chain CDR3)

<400> SEQUENCE: 37

Gln Gln Val Leu Ser Ser Pro Tyr Thr
1               5

<210> SEQ ID NO 38
<211> LENGTH: 121
<212> TYPE: PRT
<213> ORGANISM: Artificial sequence
<220> FEATURE:
<223> OTHER INFORMATION: Humanized antibody sequence (h16C3-Abb* heavy
      chain variable)
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (51)..(66)
<223> OTHER INFORMATION: CDR2
<220> FEATURE:
<221> NAME/KEY: MISC_FEATURE
<222> LOCATION: (99)..(110)
<223> OTHER INFORMATION: CDR3

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Ala Met His Trp Val Arg Gln Ala Pro Gly Gln Arg Leu Glu Trp Met
            35                  40                  45

Gly Leu Ile Ser Thr Tyr Ser Gly Asp Thr Lys Tyr Asn Gln Asn Phe
    50                  55                  60

Gln Gly Arg Val Thr Met Thr Val Asp Lys Ser Ala Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 39
<211> LENGTH: 108
<212> TYPE: PRT
<213> ORGANISM: Artificial sequence
<220> FEATURE:
<223> OTHER INFORMATION: Humanized antibody sequence (h16C3-Abb* light
      chain)
<220> FEATURE:
<221> NAME/KEY: MISC_FEATURE
<222> LOCATION: (24)..(34)
<223> OTHER INFORMATION: CDR1
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (89)..(97)
<223> OTHER INFORMATION: CDR3

<400> SEQUENCE: 39

Asp Ile Gln Met Thr Gln Ser Pro Ser Ser Leu Ser Ala Ser Val Gly
1               5                   10                  15

-continued

```
Asp Arg Val Thr Ile Thr Cys Gln Ala Ser Glu Asn Ile Tyr Gly Ala
            20              25              30

Leu Asn Trp Tyr Gln Arg Lys Pro Gly Lys Ser Pro Lys Leu Leu Ile
        35              40              45

Tyr Gly Ala Ser Asn Leu Ala Thr Gly Met Pro Ser Arg Phe Ser Gly
    50              55              60

Ser Gly Ser Gly Thr Asp Tyr Thr Phe Thr Ile Ser Ser Leu Gln Pro
65              70              75              80

Glu Asp Ile Ala Thr Tyr Tyr Cys Gln Gln Val Leu Ser Ser Pro Tyr
            85              90              95

Thr Phe Gly Gly Gly Thr Lys Leu Glu Ile Lys Arg
            100             105
```

METHODS AND COMPOSITIONS FOR TARGETING TREG CELLS

CROSS-REFERENCE TO RELATED APPLICATION

This application is a U.S. National Phase Application submitted under 35 U.S.C. 371 based on International Application No. PCT/US2019/017870, filed Feb. 13, 2019 (published as WO/2019/160970 on Aug. 22, 2019), which claims the benefit of U.S. Provisional Application No. 62/630,084, filed Feb. 13, 2018, each and all of which are hereby incorporated by reference in their entirety.

SEQUENCE LISTING INFORMATION

The instant application contains a Sequence Listing which has been submitted in ASCII format via EFS-Web and is hereby incorporated by reference in its entirety. Said ASCII copy, created on Aug. 12, 2020, is named "114382o4601.txt" and is 32,598 bytes in size.

BACKGROUND

Increased levels of $CD4^+CD25^{high}$ regulatory T cells (Tregs) have been reported in hematologic malignancies (Beyer M et al. Blood 2005, 106, 2018; Motta M et al. Leukemia 2005, 19:1788; Yang Z Z et al. Blood, 2006, 107:3639) and in patients with non-small cell lung carcinoma (Woo et al. Cancer Res 2001, 61:4766), malignant melanoma (Javia et al. J Immunother. 2003, 26:85), gastrointestinal malignancies (Sasada et al. Cancer, 2003:98:1089), ovarian cancer (Curiel J T et al. Nat Med 2004, 10:942), squamous cell carcinoma of the head and neck (Schaefer et al. Br. J. Cancer 2005, 92:913), hepatocellular carcinoma (Ormandy L A et al. Cancer Res, 2005:2457), breast cancer (Liyanage U Y et al. J Immunol, 2002, 169:2756), pancreatic cancer (Liyanage U Y et al. J Immunol, 2002, 169:2756), mesothelioma (Delong P, et al. Cancer Bio Ther 2006, 4:342), metastatic renal cell carcinoma (Dannull J et al. J Clin Invest, 2005, 115: 3623) and prostatic cancer (Vergati M et al. Cancer Immunol Immunother. 2011, 60:197). This increase has been shown in both the tumor microenvironment and in the peripheral blood. A recent study (Miller A M, et al. J Immunol 2066, 177:7398) reported elevated levels of Tregs in the peripheral blood of patients with prostrate cancer following prostatectomy, and showed in vitro the immunosuppressive function of these Tregs.

Clinical studies in patients with melanoma have shown that Tregs can inhibit both antigen-specific and non-specific T cell responses (Mukhetji B. J Exp Med. 1989, 169:1961; Chakraborty N G et al. J Immunol 1990, 145:2359). In patients with ovarian cancer, a direct correlation has been shown between tumor-infiltrating Tregs and overall survival (Curiel J T et al. Nat Med 2004, 10:942). In these patients, treatment with the recombinant interleukin 2 diphtheria toxin conjugated $DAB_{389}IL2$ (denileukin diftitox, ONTAK) led to the depletion of Tregs and improved antitumor response (Barnett B et al. Am J Reprod Immunol 2005, 54:369). Denileukin diftitox ($DAB_{389}IL-2$, ONTAK) is a fusion protein of human IL-2 and the enzymatically active and membrane-translocating domains of diphtheria toxin. It preferentially binds to cells expressing the high-affinity IL-2R, consisting of CD25 (IL-2Ra), CD122 (IL-2Rf3), and CD132 ($\gamma_c$). After binding to the IL-2R, denileukin diftitox is internalized by endocytosis and inhibits protein synthesis, ultimately leading to cell death. Denileukin diftitox has also been shown to significantly reduce the number of Tregs in peripheral blood of patients with metastatic renal cell carcinoma and to abrogate Tregs mediated immunosuppression in vivo (Dannull J et al. J Clin Invest, 2005, 115: 3623).

In summary, it has been shown that $CD4^+CD25^{high}$ regulatory T cells could reduce the efficacy of immunotherapeutic protocols and depletion of these cells could enhance vaccine medicated antitumor immune responses and overall survival (Dannull J et al. J Clin Invest, 2005, 115: 3623; Vergati M et al. Cancer Immunol Immunother. 2011, 60:197; Antony P A, et al. J Immunother 2002, 25:202).

Cancer represents one of the most frequent causes of mortality worldwide, with an estimated twenty million new cases expected annually as early as 2025 (Ferlay et al., 2015). Conventional methods of treating cancer such as surgery, radiation, and chemotherapy often elicit severe side-effects yet fail to cure the majority of patients with advanced disease, leading to relapse (Bodey et al., 1996). More recent treatment modalities have been developed to selectively target cancerous cells while largely sparing normal healthy tissues. Among them, immunotherapy has become an important treatment option for cancer patients as it revolutionizes the field of cancer medicine.

An underlying principle of cancer immunotherapy is known as immunoediting (Mittal et al., 2014), which is an extrinsic mechanism of cancer suppression that initiates only after cellular transformation has occurred and intrinsic mechanisms of cancer suppression have failed. The immunoediting process occurs in three phases; elimination, equilibrium, and escape. During the elimination and equilibrium phases, respectively, immune rejection of cancer cells either predominates or balances with cancer cell proliferation to control malignant growth. In the escape phase, however, cancer cells once held in check may escape immune recognition due to insensitivity to immune effector mechanisms and/or induction of immune suppression in the tumor microenvironment. Cancer cells that escape immune recognition are then able to more freely proliferate and grow into clinically apparent disease (Dunn et al., 2004). The aim of cancer immunotherapy is to keep cancer cells in the elimination and/or equilibrium phase by generating and/or amplifying antitumor immune responses to counteract tumor growth, delay tumor recurrence, and prolong survival (Carter, 2001; Hodge et al., 2006; Vergati et al., 2010; Gabitzsch et al., 2015). Therapeutic approaches include treating patients with checkpoint inhibitory antibodies, antitumor vaccines, and chimeric antigen receptor (CAR)-T cells, all of which leverage adaptive immunity by T cells. However, innate immunity can also generate and potentiate antitumor responses, and tumor-targeting monoclonal antibodies (mAbs) can be used to stimulate innate antitumor immunity (Topalian et al., 2011).

NEO-201 is a novel humanized IgG1 mAb that was generated against the Hollinshead allogeneic colorectal cancer vaccine platform (Hollinshead et al., 1970; Hollinshead et al., 1972). The immunogenic components of this vaccine were tumor-associated antigens (TAAs) that were derived from tumor membrane fractions pooled from surgically resected specimens from 79 patients with colon cancer (Hollinshead et al., 1985). These membrane fractions were semi-purified, screened for delayed-type hypersensitivity (DTH) in colon cancer patients versus healthy volunteers, and evaluated in clinical trials in patients with refractory colorectal cancer (Hollinshead et al., 1985; Hollinshead, U.S. Pat. No. 4,810,781, 1989; Bristol & Kantor, U.S. Pat. No. 7,829,678, 2010). These trials reported clinical benefit as defined by both antitumor response and significant prolongation in overall survival in patients that developed a sustained IgG response in addition to a cell-mediated response against the vaccine, thereby suggesting that the vaccine contained immunogenic components capable of generating antitumor antibodies (Hollinshead, 1991). This original colorectal cancer vaccine was used to generate monoclonal antibodies in mice, yielding the previously described ensituximab (NPC-1C/NEO-102) (Luka et al., 2011; Patel et al., 2013; Beg et al., 2016; Kim et al, 2017) and NEO-201. Prior work has indicated that NEO-201 binds a tumor-associated variants of CEACAM family members, particularly cancer-associated variants of CEACAM5 and CEACAM6 (Zeligs et al., 2017).

The human carcinoembryonic antigen (CEA) family is a composed of 29 genes tandemly arranged on chromosome 19q13.2. Based on nucleotide homologies, these genes are classified into two major subfamilies, the CEACAM and pregnancy-specific glycoprotein subgroups. The CEACAM-encoded proteins include CEA (CEACAM5), CEA-related cell adhesion molecules (CEACAM1, CEACAM3, CEACAM4, CEACAM6, CEACAM7 and CEACAM8. CEACAM family belongs to the Ig superfamily. Structurally, each of the human CEACAMs contain one N-terminal domain that includes 108-110 amino acid and is homologous to Ig variable domains, followed by a different number (zero to six) of Ig C2-type constant-like domains. The CEACAM proteins can interact homophilically and heterophilically with each other. CEACAM1 is a unique protein within this family because it contains an ITIM (immunoreceptor tyrosine-based inhibitory motif) like PD1 in its cytoplasmic domain. This inhibitory effect is triggered by phosphorylation of tyrosine residues with the ITIM, which results in recruitment of the Src homology 2 domain-containing tyrosine phosphatase-1 and -2. The CEACAM1 protein is expressed on a variety of immune cells including monocytes, granulocytes, activated T cells, B cells and NK cells. CEACAM1 occurs as several isoforms, the two major ones being CEACAM1-L and CEACAM1-S that have long (L), or short (S) cytoplasmic domains, respectively. CEACAM1-S expression is totally lacking in human leukocytes. CEACAM1-L is expressed on subpopulation of activated human NK cells that are negative for CD16 but positive for CD56.

Monoclonal antibodies (mAbs) consist of a unique antigen-binding region (fragment antigen-binding, Fab) that is specific to a given mAb, and a constant region (fragment crystallizable, Fe) that is common to all mAbs of the same isotype. The Fc region is capable of modulating immune cell activity by engaging with Fc receptor (FcR) family members expressed on the surface of specific immune cell types. In particular, human IgG1 mAbs can interact with Fc gamma receptor IIIa (FcγRIIIa, CD16) expressed on macrophages and NK cells. This interaction can stimulate macrophages to phagocytose mAb-opsonized cancer cells, and can activate NK cells to degranulate and lyse cancer cells through a mechanism known as antibody-dependent cellular cytotoxicity (ADCC). ADCC has been shown to be a key mediator of antitumor effects in vivo in many preclinical studies, and plays an important role in the mechanism-of-action of several mAbs used for cancer therapy (Seidel et al., 2013). Examples of clinically-approved mAbs, that can mediate ADCC, include trastuzumab, which targets the HER2 receptor for breast cancer (Seidel et al., 2013; Petricevic et al., 2013); rituximab, which targets the pan-B-cell marker CD20 for lymphoma (Seidel et al., 2013; Dall'Ozzo et al., 2004); cetuximab, which targets the epidermal growth factor receptor (EGFR) for colorectal and head and neck cancer (Seidel et al., 2013; Levy et al., 2009; Kawaguchi et al., 2007; Lopez-Albaitero et al., 2009); and avelumab, which targets the immunosuppressive ligand PD-L1 for Merckel cell carcinoma and bladder cancer (Boyerinas et al., 2015). Additionally, the Fc region can potentially interact with the C1 complex to activate complement-dependent cellular cytotoxicity (CDC), in which a proteolytic cascade culminates in the formation of pores in the plasma membrane that cause the lysis of cells targeted by the antibody. Even in instances when anti-tumor CDC has been demonstrated in vitro, there is controversy whether it is crucial for the clinical efficacy of mAb therapy in cancer (Meyer et al., 2014).

Applicant's prior U.S. Pat. Nos. 5,688,657, 7,314,622, 7,491,801, 7,763,720, 7,829,678, 8,470,326, 8,524,456, 8,535,667, 8,802,090, 9,034,588, 9,068,014, 9,371,375, 9,592,290, 9,718,866, and RE39,760, each of which is hereby incorporated by reference in its entirety, disclose various anti-cancer antibodies, cancer antigens, and related technologies.

BRIEF DESCRIPTION

We have previously shown NEO-201 to bind to cancer-associated variants of CEACAM5 and CEACAM6, specifically via a cancer-associated glycosylation variant of these proteins. NEO-201 is a humanized IgG1 monoclonal antibody that was derived from an immunogenic preparation of tumor-associated antigens from pooled allogeneic colon tumor tissue extracts. NEO-201 is reactive against a majority of tumor tissues from many different carcinomas, but is not reactive to the majority of the normal tissues. Functional analysis revealed that NEO-201 is capable of mediating both antibody-dependent cellular cytotoxicity (ADCC) and complement-dependent cytotoxicity (CDC) against tumor cells. Previous studies have demonstrated that NEO-201 attenuates the grown of human tumor xenografts in mice, and demonstrates safety and tolerability in non-human primates with a transient decrease in circulating neutrophils being the only adverse effect observed.

Applicants have herein shown that NEO-201 binds to Treg cells, and thereby can be used for purification of Treg cells, e.g., active Treg cells, and also to kill Treg cells. These results were particularly unexpected, as the NEO-201 antigens (cancer-associated glycosylated variants of CEACAM5 and CEACAM6) are believed not to be expressed by Treg cells. Based on these results, the nature of the NEO-201 antigen is being reevaluated. Without intent to be limited by theory, it is believed that Treg cells may express one or more proteins at the cell surface having glycosylation the same as or similar to the cancer-associated glycosylation of CEACAM 5/6 that constitutes the NEO-201 antigen.

Treg cell infiltration has been associated with numerous cancer types, and several studies have shown the selective ablation of Treg cells to promote anti-cancer immune responses. The newly described ability of NEO-201 to kill Treg cells supports the use of NEO-201 to potentiate anti-cancer immune responses, regardless of NEO-201 antigen expression by the cancer itself. For example, NEO-201 is expected to potentiate vaccine medicated antitumor immune responses. Use of NEO-201 to selectively ablate Treg cells may be beneficial in other diseases in which Treg cells are believed or suspected to play a role, including neurodegenerative conditions (such as Alzheimer's disease, Parkinson's disease, amyotrophic lateral sclerosis (ALS), and multiple sclerosis (MS)).

Additionally, NEO-201 binding can be used for purification of Treg cells, whether for research or therapeutic use. The defective suppressive function of human Tregs appears to be a common feature of autoimmune diseases and conditions. Purification of Treg cells may have diagnostic and/or therapeutic utility. For example, purified Treg cells from a healthy donor may be transplanted to an individual having an autoimmune condition in order to treat that condition. Additionally, purified autologous or heterologous Tregs may be engineered and introduced into a patient for the treatment of an autoimmune disease.

The working examples describe experiments conducted using PBMCs from normal donors for phenotypic and functional analysis. The EasySep™ StemCell Treg isolation kits and anti-biotin kits were utilized with either manufacture-provided Treg purification reagents or customized using biotin-labelled NEO-201 mAb to isolate Tregs from PBMCs. Phenotypic analysis was conducted by flow cytometry for the following markers: CD4, CD25, CD127, FoxP3, CD15s, CD45RA, CCR4, NEO-201 antigen, CEACAM5, and CEACAM6. The ability of NEO-201-isolated Tregs to suppress autologous CD4+T responder cell proliferation was assessed using a Treg co-culture suppression assay. The percentage of NEO-201+ cells in the population of CD4+CD25highCD127-FoxP3+CD15s+CCR4+Tregs ranged from 61.8% to 81.9%. NEO-201+Tregs were CD45RA−. Isolated CD4+NEO-201+Tregs were capable of suppressing CD4+T responder cell proliferation.

Additionally, and the ability of NEO-201 to mediate the killing of opsonized Tregs was evaluated using a CDC assay. The NEO-201 mAb was demonstrated to be capable of mediating CDC activity against Tregs.

From these results it is concluded that NEO-201 reacts against human Tregs and can be used as a novel marker for the identification and purification of Tregs. Tregs isolated using the NEO-201 mAb were functionally suppressive, and could be eliminated by CDC. Based on the ability of the antibody to bind Treg cells, in ADCC-mediated Treg cell killing should also occur. This application demonstrates for the first time that this anticancer drug may also have utility in targeting Treg-mediated immunosuppression of antitumor immunity.

BRIEF DESCRIPTION OF THE SEVERAL VIEWS OF THE DRAWINGS

FIG. 1: Isolation of functional Treg cells by NEO-201. Percentage of functional Tregs isolated using commercial kit (Human CD4+CD127lowCD25+) or selection based on NEO-201 expression. The EasySep™ Human CD4+CD127lowCD25+ Regulatory T Cell Isolation kit yielded 67.14% active Treg cells, while selection based on NEO-201 positive expression yielded 99.12% active Treg cells.

FIG. 2: Regulatory T-cells are CEACAM-5 and CEACAM-6 negative as determined by flow cytometry. Phenotypic analysis of isolated T-regs (EasySep™ Human CD4+CD127lowCD25+ Regulatory T Cell Isolation kit (HD 19). Cells were stained with PE Mouse Anti-Human CD66 antibody (Clone B1.1/CD66) which recognizes CD66a (CEACAM1), CD66c (CEACAM6), CD66d (CEACAM3) and CD66e (CEACAM5). 44.84% of CD4+/CD25high/CD127−/FOXp3+ cells are NEO-201+/CEACAM5− and CEACAM6− cells.

FIG. 3. NEO-201 mediates CDC against CD4$^+$ CD15s$^+$ Tregs. Treg cells express CD4 and CD15s (sialyl Lewis X glycan). Complement alone did not kill Tregs. NEO-201 mediated CDC against Treg cells. Reduced the population of CD4+CD15s+ Tregs by 53.4%. Procedure: CD4+ T cells were isolated from PBMCs. Cells were treated −/+NEO-201 mAb (10 µg/mL). Cells were then treated −/+complement (1:8 dilution, 2 hr). Cells were washed and stained for CD4 and CD15s markers. Marker expression was measured by flow cytometry.

DETAILED DESCRIPTION

In one aspect, the disclosure provides a method of killing Treg cells in vivo, comprising administering an effective amount of a NEO-201 antibody to a patient.

In another aspect, the disclosure provides a method of potentiating anti-cancer immune responses in a patient, comprising administering an effective amount of a NEO-201 antibody to said patient.

The method may further comprise administering a cancer vaccine to said patient. Exemplary cancer vaccines that may be administered are disclosed in, e.g., Fisher et al., Immun Inflamm Dis. 2017 March; 5(1): 16-28; Klages et al., Cancer Res Oct. 15, 2010 (70) (20) 7788-7799; Reginato et al., Br J Cancer. 2013 Oct. 15; 109(8): 2167-2174; Litzinger M T et al., Blood 2007, 110:3192, each of which is hereby incorporated by reference in its entirety.

In another aspect, the disclosure provides a method of decreasing Treg cell infiltration in a cancer in a patient, comprising administering an effective amount of a NEO-201 antibody to said patient.

In another aspect, the disclosure provides a method of stimulating cancer regression in a patient, comprising administering an effective amount of a NEO-201 antibody to said patient, thereby activating, enhancing, or stimulating anti-cancer immunity in said patient.

Said cancer may not express CEACAM5 or CEACAM6.

Said method may further comprise, prior to or at the time of said administering, determining that said cancer is CEACAM5 and CEACAM6 negative, which optionally may be determined by testing for the expression of CEACAM5 and CEACAM6 protein, e.g., by staining with antibodies specific for CEACAM5 and/or CEACAM6, such as cross-reactive antibodies that specifically bind to both CEACAM5 and CEACAM6.

In another aspect, the disclosure provides a method of treating or preventing cancer, decreasing the burden of cancer, or slowing the growth or proliferation rate of cancer, comprising administering an effective amount of a NEO-201 antibody to a patient in need thereof, wherein said cancer is CEACAM5 and CEACAM6 negative.

Said method may further comprise administering another therapeutic agent to said patient. Said other agent may be selected from (a) microtubule inhibitors, topoisomerase inhibitors, platins, alkylating agents, and anti-metabolites; (b) MK-2206, ON 013105, RTA 402, BI 2536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and/or vinorelbine; (c) 1-D-ribofuranosyl-1,2,4-triazole-3 carboxamide, 9->2-hydroxy-ethoxy methylguanine, adamantanamine, 5-iodo-2r-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir; (d) a PD-1 inhibitor or anti-PD-1 antibody such as KEYTRUDA® (pembrolizumab) or OPDIVO® (nivolumab), or (e) a CTLA-4 inhibitor or anti-CTLA-4 antibody such as YERVOY® ipilimumab. It is predicted that the combination of immune checkpoint inhibition (PD-1 inhibition and/or CTLA-4 inhibition) with Treg ablation may be particularly efficacious for cancer therapy. See Vargas et al., Immunity. 2017 Apr. 18; 46(4): 577-586 and Taylor et al., J Clin Invest. 2017; 127(9):3472-3483, each of which is hereby incorporated by reference in its entirety.

Said NEO-201 antibody may elicit or increase an anti-cancer immune response in the patient.

In another aspect, the disclosure provides a method of killing Treg cells in vitro, comprising contacting said Treg cells with a NEO-201 antibody. Said method may further comprise contacting said Treg cells with complement. Said Treg cells may be killed by CDC. Said method may further comprise contacting said Treg cells with effector cells, such as natural killer cells. Said Treg cells may be killed by ADCC.

In another aspect, the disclosure provides a method of killing Treg cells ex vivo, comprising contacting a sample comprising Treg cells with an effective amount of a NEO-201 antibody. Said sample may be obtained from a patient.

Said NEO-201 antibody may be coupled to a cytotoxic moiety.

In another aspect, the disclosure provides a method of detecting Treg cells, comprising detecting the expression of the NEO-201 antigen by said Treg cells, optionally wherein the level of Treg cells in a patient sample, such as a blood or biopsy sample, is used to diagnose cancer or determine cancer prognosis. Optionally said method may further comprise assigning or administering treatment to a patient based on the detection of Treg cells. For example, the patient may be assigned to be administered or may be administered NEO-201 in an amount effective to kill Treg cells if Treg cells are detected in said patient sample.

Said method may comprise contacting said Treg cells with a NEO-201 antibody.

Said detecting may comprise cell sorting, optionally fluorescence activated cell sorting.

In another aspect, the disclosure provides a method of detecting Treg cells, comprising contacting cells with a NEO-201 antibody and detecting cells that express NEO-201. Said NEO-201 antibody may be directly or indirectly labeled.

In another aspect, the disclosure provides a method of staining Treg cells, comprising contacting cells with a NEO-201 antibody. Said NEO-201 antibody may be directly or indirectly labeled.

In another aspect, the disclosure provides a method of isolating Treg cells, comprising isolating cells that express the NEO-201 antigen. Said method may comprise contacting a sample containing Treg cells with a NEO-201 antibody, optionally wherein said NEO-201 antibody is directly or indirectly labeled. Said sample may be or may comprise blood or bone marrow. Said method may comprise separating NEO-201 positive Treg cells from NEO-201 negative cells. Said method may further comprise genetically modifying said Treg cells, and optionally introducing said cells into said patient or another individual.

Said Treg cells may be isolated by cell sorting, optionally fluorescence activated cell sorting.

Said Treg cells may be isolated by contacting sample with a support comprising a NEO-201 antibody, whereby said Treg cells are retained on said support.

Said methods of staining or detecting may further comprising detecting the expression of another marker or combination of markers whose presence, absence, and/or level of expression are indicative of Treg cells, e.g., CD4+, CD15s+, FoxP3+, CD25+, CCR4+ and/or $CD127^{low}$ or CD127−, such as CD4+CD15s+, CD4+ FoxP3+CD25+, or CD4+ FoxP3+ CD25+$CD127^{low}$, in combination with NEO-201. For example, cells that are NEO-201+CD4+CD15s+; NEO-201+CD4+CD15s+ FoxP3+CD25+; NEO-201+CD4+ CD15s+ FoxP3+CD25+$CD127^{low}$; NEO-201+CD4+ FoxP3+CD25+; or NEO-201+CD4+ FoxP3+CD25+ $CD127^{low}$; preferably NEO-201+CD4+CD15s+; or preferably NEO-201+CD4+$CD127^{low}$ CD25+; or preferably CD4+$CD25^{high}$ CD127− FoxP3+CD15s+ CCR4+ may be identified, detected, isolated, and/or purified as Treg cells in accord with the methods disclosed herein.

In any of the foregoing or following methods, said NEO-201 antibody may comprise at least one, two, three, four, five, or preferably all six of the CDR sequences contained in SEQ ID NO: 28 and SEQ ID NO: 29.

In any of the foregoing or following methods, said NEO-201 antibody may comprise a variable heavy chain sequence having at least 90% identity to SEQ ID NO: 38.

In any of the foregoing or following methods, said NEO-201 antibody may comprise a variable light chain sequence having at least 90% identity to SEQ ID NO: 39.

In any of the foregoing or following methods, said NEO-201 antibody may comprise a variable heavy chain sequence having at least 90% identity to SEQ ID NO: 38 and a variable light chain sequence having at least 90% identity to SEQ ID NO: 39.

In any of the foregoing or following methods, said NEO-201 antibody may comprise a heavy chain sequence having at least 90% identity to amino acids 20-470 of SEQ ID NO: 28 and a light chain sequence having at least 90% identity to amino acids 20-233 of SEQ ID NO: 29.

In any of the foregoing or following methods, said NEO-201 antibody may comprise all six of the CDR sequences contained in SEQ ID NO: 28 and SEQ ID NO: 29.

In any of the foregoing or following methods, said NEO-201 antibody may comprise a human IgG1 constant domain. Alternatively, said NEO-201 antibody may comprise a human IgG2, human IgG3, or human IgG4 constant domain, or a hybrid or chimeric domain comprising two or more of human IgG1, IgG2, IgG3, or IgG4.

In any of the foregoing or following methods, said NEO-201 antibody may be humanized.

In any of the foregoing or following methods, said NEO-201 antibody may be conjugated to another moiety.

In any of the foregoing or following methods, said NEO-201 antibody may be conjugated to another cytotoxic moiety, label, radioactive moiety, or affinity tag.

In any of the foregoing or following methods, said NEO-201 antibody may compete with the antibody contained in SEQ ID NO: 28 and SEQ ID NO: 29 for binding to the NEO-201 antigen.

In any of the foregoing or following methods, said cancer may be selected from hematologic malignancies, lung cancer such as non-small cell lung carcinoma, melanoma, gastrointestinal malignancies, ovarian cancer, squamous cell carcinoma of the head and neck, hepatocellular carcinoma, breast cancer, pancreatic cancer, mesothelioma, metastatic renal cell carcinoma, and prostatic cancer. Said cancer may comprise Treg cells.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting.

As used in the description herein and throughout the claims that follow, the meaning of "a," "an," and "the" includes plural reference unless the context clearly dictates otherwise.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "NK-depleted" or "natural killer-depleted" as used herein refer to a patient having low natural killer (NK) cell levels relative to the normal range. NK cells are a cytotoxic innate immune lymphocyte. Typically, NK cells comprise 5-20% of the peripheral blood mononuclear cells (PBMCs) in a healthy individual. A patient having NK cells comprising less than 5% of the PMBCs is referred to as NK-depleted. Additionally, a patient is referred to as severely NK-cell depleted if NK cells comprising less than 3% of the PMBCs. Additionally, in normal individuals, up to 90% of PBMC NK cells are $CD56^{dim}CD16^+$ NK cells, and these are considered the most cytotoxic subset. If less than 70% of PBMC NK cells are $CD56^{dim}CD16^+$ NK cells, then the patient is referred to as NK-depleted. Additionally, if less than 50% of PBMC NK cells are $CD56^{dim}CD16^+$ NK cells, then the patient is referred to as severely NK-depleted. A given patient may be referred to as NK-depleted or severely NK-depleted based on meeting either or both of these individual criteria. Generally speaking, a patient's status as NK-depleted or severely NK-depleted is determined by testing a sample taken from the patient, e.g., a blood sample, e.g., a sample obtained and tested within one or two weeks prior. A patient's status as NK-depleted or severely NK-depleted may also be inferred from a disease diagnosis and/or a course of treatment that is associated with such depletion of NK cells.

"Antibody," as used herein, refers broadly to any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, from all sources, e.g., human, rodent, rabbit, cow, sheep, pig, dog, chicken, are considered to be "antibodies." Antibodies include but are not limited to chimeric antibodies, human antibodies and other non-human mammalian antibodies, humanized antibodies, single chain antibodies (scFvs), camelbodies, nanobodies, IgNAR (single-chain antibodies derived from sharks), small-modular immunopharmaceuticals (SMIPs), and antibody fragments (e.g., Fabs, Fab', F(ab')$_2$.) Numerous antibody coding sequences have been described; and others may be raised by methods well-known in the art. See Streltsov, et al. (2005) *Protein Sci.* 14(11): 2901-9; Greenberg, et al. (1995) *Nature* 374(6518): 168-173; Nuttall, et al. (2001) *Mol Immunol.* 38(4): 313-26; Hamers-Casterman, et al. (1993) *Nature* 363(6428): 446-8; Gill, et al. (2006) *Curr Opin Biotechnol.* 17(6): 653-8.

"NEO-201 antibody" refers to an antibody containing the heavy and light chains of SEQ ID NOs: 28 and 29 or the variable regions optionally together with the constant regions contained therein, as well as fragments and variants thereof. Such variants include sequences containing one, two, three, four, five or preferably all six of the CDR sequences contained in SEQ ID NO: 28 and SEQ ID NO: 29, i.e., the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37. Such variants also include antibodies that compete with NEO-201 for binding to the NEO-201 antigen. Said antibody may be humanized. Said antibody may be expressed containing one or more leader sequences, which may be removed during expression and/or processing and secretion of the antibody. Said antibody may be presented in a monovalent, bivalent, or higher multivalent format, including without limitation a bispecific or multispecific antibody containing said NEO-201 antibody sequence and a binding fragment of a different antibody. Typically said antibody specifically binds to carcinoma cells and competes for binding to carcinoma cells with an antibody comprising the variable heavy chain of SEQ ID NO: 38 and variable light chain of SEQ ID NO: 39, or comprising the heavy chain of SEQ ID NO: 28 and light chain of SEQ ID NO: 29. One or more of those CDR sequences contained in SEQ ID NO: 28 and/or SEQ ID NO: 29 may be substituted with a variant sequence, such as the light chain CDR1 of SEQ ID NO: 1 or 4; light chain CDR2 of SEQ ID NO: 2 or 5; light chain CDR3 of SEQ ID NO: 3 or 6; heavy chain CDR1 of SEQ ID NO: 7; heavy chain CDR2 of SEQ ID NO: 8, 10, 30, or 31; heavy chain CDR3 of SEQ ID NO: 9 or 11; or SEQ ID NOs: 30-31. The light chain may comprise the CDRs contained in the light chain sequence of SEQ ID NO: 14, 16, 17, 18, 19, 20, 21, or 29. The heavy chain may comprise the CDRs contained in the heavy chain sequence of SEQ ID NO: 15, 22, 23, 24, 25, 26, 27, or 29. Said antibody may comprise a variable heavy chain sequence having at least 75%, 80%, 85%, 90%, 95%, 96%, 97%, 98%, or 99% identity to SEQ ID NO: 38, and/or a variable light chain sequence having at least 75%, 80%, 85%, 90%, 95%, 96%, 97%, 98%, or 99% identity to SEQ ID NO: 39, optionally wherein said heavy and/or light chain sequence contains one, two, three, four, five or preferably all six of the CDR sequences contained in SEQ ID NO: 28 and SEQ ID NO: 29, i.e., the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37. Said antibody may be conjugated to another moiety, such as a cytotoxic moiety, radioactive moiety, label, or purification tag.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. Antigens may be tumor specific (e.g., expressed by neoplastic cells of pancreatic and colon carcinoma.)

"Cancer," as used herein, refers broadly to any neoplastic disease (whether invasive or metastatic) characterized by abnormal and uncontrolled cell division causing malignant growth or tumor.

"Cancer vaccine," as used herein, refers to an immunogenic composition that elicits or is intended to elicit an immune response against a cancer cell.

"Chimeric antibody," as used herein, refers broadly to an antibody molecule in which the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug; or the variable region, or a portion thereof, is altered, replaced or exchanged with a variable region having a different or altered antigen specificity.

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) "*Sequences of Proteins of Immunological Interest*" National Institutes of Health, Bethesda, MD These expressions include the hypervariable regions as defined by Kabat, et al. (1983) "*Sequences of Proteins of Immunological Interest*" U.S. Dept. of Health and Human Services or the hypervariable loops in 3-dimensional structures of antibodies. Chothia and Lesk (1987) *J Mol. Biol.* 196: 901-917. The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction. Kashmiri (2005) *Methods* 36: 25-34.

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/nil) or a relative amount (e.g., relative intensity of signals).

"Differentially present," as used herein, refers broadly to differences in the quantity or quality of a marker present in a sample taken from patients having a disease or condition as compared to a comparable sample taken from patients who do not have one of the diseases or conditions. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker may be considered to be differentially present. Optionally, a relatively low amount of up-regulation may serve as the marker.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," as used herein refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that achieves a desired result. An "effective amount" when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this disclosure.

"Expression vector," as used herein, refers broadly to any recombinant expression system for the purpose of expressing a nucleic acid sequence of the present disclosure in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Framework region" or "FR," as used herein, refers broadly to one or more of the framework regions within the variable regions of the light and heavy chains of an antibody. See Kabat, et al. (1987) "*Sequences of Proteins of Immunological Interest*," National Institutes of Health, Bethesda, MD These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"High affinity," as used herein, refers broadly to an antibody having a KD of at least $10^{-8}$ M, more preferably at least $10^{-9}$ M and even more preferably at least $10^{-10}$ M for a target antigen. However, "high affinity" binding can vary for other antibody isotypes. For example, "high affinity" binding for an IgM isotype refers to an antibody having a KD of at least $10^{-7}$ M, more preferably at least $10^{-8}$ M.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison. The term "sequence identity" may be used interchangeably with "homology."

"Host cell," as used herein, refers broadly to a cell that contains an expression vector and supports the replication or expression of the expression vector. Host cells may be prokaryotic cells such as *E. coli*, or eukaryotic cells such as yeast, insect (e.g., SF9), amphibian, or mammalian cells such as CHO, HeLa, HEK-293, e.g., cultured cells, explants, and cells in vivo.

"Hybridization," as used herein, refers broadly to the physical interaction of complementary (including partially complementary) polynucleotide strands by the formation of hydrogen bonds between complementary nucleotides when the strands are arranged antiparallel to each other.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction. The term "KD", as used herein, is intended to refer to the dissociation constant, which is obtained from the ratio of Kd to Ka (i.e., Kd/Ka) and is expressed as a molar concentration (M). KD values for antibodies can be determined using methods well established in the art.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Isolated," as used herein, refers broadly to material removed from its original environment in which it naturally occurs, and thus is altered by the hand of man from its natural environment. Isolated material may be, for example, exogenous nucleic acid included in a vector system, exogenous nucleic acid contained within a host cell, or any material which has been removed from its original environment and thus altered by the hand of man (e.g., "isolated antibody").

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al. (2002) *Short Protocols in Molecular Biology* ($5^{th}$ Ed.) John Wiley & Sons, NY. Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

The term "low level" or "low" as used in relation to a marker such as CD127 is well known in the art and refers to the expression level of the cell marker of interest (e.g., CD 127), in that the expression level of the cell marker is low by comparison with the expression level of that cell marker in other cells in a population of cells being analyzed as a whole. More particularly, the term "low" refers to a distinct population of cells that express the cell marker at a lower level than one or more other distinct population of cells. Accordingly $CD127^{low}$ refers to cells of a type that stains slightly or dully when contacted with a labeled CD127 antibody, e.g., at a level that is higher than a CD127− subpopulation but lower than the CD127+ subpopulation.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, and tapirs. Mammals include but, are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington DC "Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. *Antigens (Chapter 3)* Immunology (5$^{th}$ Ed.) New York: W.H. Freeman and Company, pages 57-75.

"Patient," as used herein, refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient". In preferred embodiments of the inventions disclosed herein, the patient is a human.

"Polypeptide," "peptide" and "protein," are used interchangeably and refer broadly to a polymer of amino acid residues. The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins.

The terms "polypeptide," "peptide" and "protein" include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologics. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. See, e.g., Turner, et al. (1987) *CSH Symp. Quant. Biol.* LII: 123-33; Frier, et al. (1986) *PNAS* 83: 9373-77; Turner, et al. (1987) *J. Am. Chem. Soc.* 109: 3783-85. A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence. "Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials. Exemplary solid supports include beads, such as activated beads, magnetically responsive beads, or fluorescently labeled beads.

"Subjects" as used herein, refers broadly to anyone suitable to be treated according to the presently disclosed inventions include, but are not limited to, avian and mammalian subjects, and are preferably mammalian. Mammals in the context of the presently disclosed inventions include, but are not limited to, canines, felines, bovines, caprines, equines, ovines, porcines, rodents (e.g., rats and mice), lagomorphs, primates, humans. Any mammalian subject in need of being treated according to the presently disclosed inventions is suitable. Human subjects of any gender and at any stage of development (i.e., neonate, infant, juvenile, adolescent, adult, elderly) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "patients." In preferred embodiments of the disclosed invention, the subject is a human.

"Symptoms" of disease as used herein, refers broadly to any morbid phenomenon or departure from the normal in structure, function, or sensation, experienced by the patient and indicative of disease.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., tumor growth, metastasis). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., tumor growth, metastasis). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., tumor growth, metastasis).

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a plasmid, cosmid, phagemid, phage DNA, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector.

The techniques and procedures are generally performed according to conventional methods well known in the art and as described in various general and more specific references that are cited and discussed throughout the present specification. See, e.g., Sambrook, et al. (2001) *Molec. Cloning: Lab. Manual* [3$^{rd}$ Ed] Cold Spring Harbor Laboratory Press. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

EXAMPLES

The invention now being generally described, it will be more readily understood by reference to the following examples, which are included merely for purposes of illustration of certain aspects and embodiments of the present invention, and are not intended to limit the invention.

Example 1

NEO-201 can Isolate Functional Treg Cells

In this example, cell sorting based on NEO-201 binding is shown to yield a high percent of functional Tregs. The percentage of functional Tregs isolated using commercial kit (Human CD4+CD127lowCD25+) or selection based on NEO-201 expression is shown in FIG. 1. The EasySep™ Human CD4+CD127lowCD25+ Regulatory T Cell Isolation kit yielded 67.14% active Treg cells, while selection based on NEO-201 positive expression yielded 99.12% active Treg cells.

Applicants have previously shown NEO-201 to bind to a cancer-associated glycoprotein variant of CEACAM5 and CEACAM6. Treg cells are not known to express CEACAM5 and CEACAM6. In order to further determine the basis of NEO-201 binding to Treg cells, the cells were tested for CEACAM5 and CEACAM6 expression by flow cytometry. Regulatory T-cells are both CEACAM-5 and CEACAM-6 negative (FIG. 2).

Methods.

Binding of human Tregs markers to isolated human Tregs was analyzed by flow cytometry. Tregs ($1.0 \times 10^6$) were incubated with 1 µL per test of LIVE/DEAD Fixable Aqua (Thermo Fisher Scientific, Waltham, MA, USA) in 1× phosphate buffered saline (PBS) for 30 min at 4° C. to accomplish live versus dead cell discrimination. Cells were then centrifuged, washed twice with cold PBS, and then stained with Pacific Blue-conjugated NEO-201 antibody, anti-CD25-APC-H7, anti-CD15s-Alexa 488, anti-CD127-APC and intra-cellular staining with anti-Foxp3-PerCP-CY5.5. (BioLegend, San Diego, CA) in 1×PBS+1% BSA (Teknova, Hollister, CA, USA) for 30 minutes at 4° C. After staining, cells were washed twice with cold PBS and examined using a FACSVerse flow cytometer (BD Biosciences, San Jose, CA, USA). Analysis of cellular fluorescence was performed using BD FACSuite software (BD Biosciences, San Jose, CA, USA). Isolation of T-regs by a commercial kit was conducted using the EasySep™ Human CD4+ CD127lowCD25+ Regulatory T Cell Isolation kit (HD 19) per the manufacturer's instructions. For analysis of CEACAM expression, cells were stained with PE Mouse Anti-Human CD66 antibody (Clone B1.1/CD66) which recognizes CD66a (CEACAM1), CD66c (CEACAM6), CD66d (CEACAM3) and CD66e (CEACAM5). 44.84% of CD4+/CD25high/CD127−/FOXp3+ cells are NEO-201+/ CEACAM5− and CEACAM6− cells.

Example 2

NEO-201 can Kill Tregs by Complement Dependent Cytotoxicity (CDC)

This example shows that NEO-201 can mediate CDC against CD4+CD15s+ Tregs. Treg cells express CD4 and CD15s (sialyl Lewis X glycan). CD4+ T cells were isolated from PBMCs, and the cells were treated −/+NEO-201 mAb (10 µg/mL). The cells were then treated −/+complement (1:8 dilution, 2 hr). The cells were then washed and stained for CD4 and CD15s markers. Marker expression was measured by flow cytometry. Complement alone did not kill Tregs. However, when Tregs were treated with both NEO-201 and complement, the population of CD4+ CD15s+ Tregs was reduced by 53.4%, indicating CDC had occurred.

Complement-Dependent Cytotoxicity (CDC) Assay Methods.

CDC assays were performed using a modification of a previously described procedure (Konishi et al., 2008). CD4+ T cells were isolated and then treated with or without 10 µg/mL NEO-201 for 15 min at 37° C. to opsonize the cells. Purified rabbit complement (MP Biomedicals, Santa Ana, CA) was then added to the cells at a 1:8 dilution. After incubation at 37° C. for 120 min, cells were washed and stained with fluorescent-labeled antibodies against CD4 and CD15s. Following 30 min incubation, cells were washed, and fluorescence was measured by flow cytometry using a BD FACSVerse. Analysis of cellular fluorescence was performed using BD FACSuite software (BD Biosciences, San Jose, CA, USA).

Example 3

Generation of the Humanized NEO-201 Monoclonal Antibody

The Hollinshead colon cancer specific vaccine was used as the immunogenic material to generate monoclonal antibodies in mice. The method for the preparation of tumor-associated proteins and peptides has been previously described (Hollinshead, U.S. Pat. No. 4,810,781, 1989). In brief, cancer tissue was minced and used to generate a single cell suspension that was then subjected to hypotonic saline membrane extraction, a series of centrifugation steps, and followed with low frequency sonication. The resulting membrane-extracted proteins were fractionated on Sephadex G-200 resin or by electrophoretic methods, then concentrated and quantitated (Hollinshead et al, 1970; Hollinshead et al., 1972; Hollinshead et al., 1985). The TAA preparation was admixed with complete Freund's adjuvant and injected subcutaneously in BALB/c mice. This was followed by 3 booster injections in incomplete Freund's adjuvant, separated by 2-3 weeks. Mouse serum was tested by ELISA for antibody responses against the immunizing antigen and mice with potent responses were used to generate immortalized hybridoma cells by fusing the mouse B cells from the spleen with the SP2/0-Ag14 myeloma cell line and selecting cells that grew and produced mouse immunoglobulins (IgGs). From these mouse IgGs, the murine 16C3 clone (m16C3) was chosen based upon reactivity with colon tumor cell membrane extract derived from LS174T or HT-29 cells as determined by ELISA. The cDNAs encoding the heavy and light chain IgG1 were determined from RNA isolated from hybridoma clone 16C3 E12 and shown to be unique (Bristol & Kantor, U.S. Pat. No. 7,829,678, 2010). The m16C3 protein sequence was humanized as h16C3 and designated NEO-201. Humanization was performed in silico by replacing mouse sequences outside the complementarity-determining regions (CDRs) of the Fab region of both heavy and light chain proteins with human Fab sequences, and retaining the three mouse CDR sequences from each chain. The Fc regions of the heavy and light chains were selected from human IgG1 isotype used in other humanized approved mAb products. The amino acid sequence was back-translated to DNA, which was optimized for protein expression in CHO cells. The DNA for heavy and light chain h16C3 was then synthesized chemically, cloned into mammalian expression plasmids, and transfected into mammalian cell lines (HEK293T and CHO). Several stable CHO cell lines expressing recombinant h16C3 were derived and banked. Purified recombinant h16C3 was retested in studies which verified that the humanized 16C3 antibody had similar characteristics as the original m16C3 antibody (Bristol & Kantor, U.S. Pat. No. 7,829,678, 2010).

The NEO-201 antibody sequences used in these examples are contained in the following illustration:

H16C3-Abb* Heavy Chain:
(SEQ ID NO: 28)
MGWSCIIFFLVATATGVHS/QVQLVQSGAEVKKPGASVKVSCKASGYTF

TDYAMHWVRQAPGQRLEWMGLISTYSGDTKYNQNFQGRVTMTVDKSAST

AYMELSSLRSEDTAVYYCARGDYSGSRYWFAYWGQGTLVTVSS/ASTKG

PSVFPLAPSSKSTSGGTAALGCLVKDYFPEPVTVSWNSGALTSGVHTFP

AVLQSSGLYSLSSVVTVPSSSLGTQTYICNVNFIKPSNTKVDKKVEPKS

CDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKS

RWQQGNVFSCSVMHEALHNHYTQKSLSLSPGK

H16C3-Abb* Light Chain:
(SEQ ID NO: 29)
MGVPTQLLLLWLTVVVVRC/DIQMTQSPSSLSASVGDRVTITCQASENI

YGALNWYQRKPGKSPKLLIYGASNLATGMPSRFSGSGSGTDYTFTISSL

QPEDIATYYCQQVLSSPYTFGGGTKLEIKR/TVAAPSVFIFPPSDEQLK

SGTASVVCLLNNFYPREAKVQWKVDNALQSGNSQESVTEQDSKDSTYSL

SSTLTLSKADYEKHKVYACEVTHQGLSSPVTKSFNRGEC

The boundaries between the expression leader sequence, variable region, and constant region is delimited by a forward slash ("/") in each sequence, and CDR sequences are shown in bold, underlined text. The antibody sequences used included the variable and constant regions shown. These include the heavy chain CDR1 of SEQ ID NO: 32, the heavy chain CDR2 of SEQ ID NO: 33, the heavy chain CDR3 of SEQ ID NO: 34, the light chain CDR1 of SEQ ID NO: 35, the light chain CDR2 of SEQ ID NO: 36, and the light chain CDR3 of SEQ ID NO: 37.

Abbreviations

Amyotrophic lateral sclerosis (ALS), Antibody-dependent cellular cytotoxicity (ADCC), area under plasma concentration-time curve from time 0 to infinity (AUCinf), dose-normalized area under the plasma concentration-time curve from time 0 to infinity (AUCinf/D), baseline (BL), complement-dependent cytotoxicity (CDC), clearance (CL), maximum observed plasma concentration (Cmax), dose-normalized measured maximum plasma concentration (Cmax/D), estrogen receptor (ER), half-life (HL), immuno-histochemistry (IHC), multiple sclerosis (MS) natural killer (NK), non-small cell lung cancer (NSCLC), peripheral blood mononuclear cells (PBMC), progesterone receptor (PR), tumor-associated antigen (TAA), time of maximum observed plasma concentration (Tmax), volume of distribution (Vz).

REFERENCES

Each document cited herein, including each one in the following list, is hereby incorporated by reference in its entirety.

1. Ferlay J, Soerjomataram I, Dikshit R, Eser S, Mathers C, Rebelo M, Parkin D M, Forman D, Bray F. Cancer incidence and mortality worldwide: sources, methods and major patterns in GLOBOCAN 2012. *Int J Cancer.* 2015 Mar. 1; 136(5):E359-86.
2. Bodey B, Siegel S E, Kaiser H E. Human cancer detection and immunotherapy with conjugated and non-conjugated monoclonal antibodies. *Anticancer Res.* 1996 March-April; 16(2):661-74.
3. Mittal D, Gubin M M, Schreiber R D, Smyth M J. New insights into cancer immunoediting and its three component phases—elimination, equilibrium and escape. Curr Opin Immunol, 2014 April; 27:16-25. doi: 10.1016/j.coi.2014.01.004.
4. Dunn G P, Old L J, Schreiber R D. The three Es of cancer immunoediting. Annu Rev Immunol. 2004; 22:329-60.
5. Carter P. Improving the efficacy of antibody-based cancer therapies. Nat Rev Cancer. 2001 November; 1(2):118-29.
6. Hodge J W, Greiner J W, Tsang K Y, Sabzevari H, Kudo-Saito C, Grosenbach D W, Gulley J L, Arlen P M, Marshall J L, Panicali D, Schlom J. Costimulatory molecules as adjuvants for immunotherapy. Front Biosci. 2006 Jan. 1; 11: 788-803.
7. Vergati M I C, Huen N Y, Schlom J, Tsang K Y. Strategies for cancer vaccine development. J Biomed Biotechnol. 2010; 2010(596432).
8. Gabitzsch E S T K, Palena C, David J M, Fantini M, Kwilas A, Rice A E, Latchman Y, Hodge J W, Gulley J L, Madan R A, Heery C R, Balint J P Jr, Jones F R, Schlom J. The generation and analyses of a novel combination of recombinant adenovirus vaccines targeting three tumor antigens as an immunotherapeutic. Oncotarget. 2015; 6(30:31344-59.
9. Topalian S L, Weiner G J, Pardoll D M. Cancer immunotherapy comes of age. J Clin Oncol. 2011 Dec. 20; 29(36):4828-36.
10. Hollinshead A, Glew D, Bunnag 13, Gold P, Herberman R. Skin-reactive soluble antigen from intestinal cancer-cell-membranes and relationship to carcinoembryonic antigens. *Lancet.* 1970; 1(7658):1191-1195.
11. Hollinshead A C, McWright C G, Alford T G D, Gold P, Herbeman R B. Separation of skin reactive intestinal cancer antigen from the carcinoembryonic antigen of Gold. *Science.* 1972; 177(4052):887-889.
12. Hollinshead A, Elias E G, Arlen M, Buda B, Mosley M, Scherrer J. Specific active immunotherapy in patients with adenocarcinoma of the colon utilizing tumor-associated antigens (TAA). A phase I clinical trial. *Cancer.* 1985; 56(3):480-489.
13. Hollinshead A C. Methods of preparing epitopes of tumor associated antigens. U.S. Pat. No. 4,810,781. 1989.
14. Bristol J A, Kantor J A. Recombinant monoclonal antibodies and corresponding antigens for colon and pancreatic cancers. U.S. Pat. No. 7,829,678. 2010.
15. Hollinshead A. Active specific immunotherapy and immunochemotherapy in the treatment of lung and colon cancer. Semin Surg Oncol. 1991 July-August; 7(4):199-210.
16. Luka J, Arlen P M, Bristol A. Development of a serum biomarker assay that differentiates tumor-associated MUC5AC (NPC-1C ANTIGEN) from normal MUC5AC. J Biomed Biotechnol. 2011; 2011:934757. doi: 10.1155/2011/934757. Epub 2010 Dec. 16. PubMed PMID: 21197415
17. Patel S P, Bristol A, Saric O, Wang X P, Dubeykovskiy A, Arlen P M, Morse M A. Anti-tumor activity of a novel monoclonal antibody, NPC-1C, optimized for recognition of tumor antigen MUC5AC variant in preclinical models. Cancer Immunol Immunother. 2013 June; 62(6):1011-9.
18. Beg M S, Azad N S, Patel S P, Torrealba J, Mavroukakis S, Beatson M A, Wang X P, Arlen P M, Morse M A. A phase 1 dose-escalation study of NEO-102 in patients with refractory colon and pancreatic cancer. Cancer Chemother Pharmacol. 2016 September; 78(3):577-84,
19. Kim R D, Arlen P M, Tsang K Y, Mavroukakis S A, Zaki A, Cui K, Azad N S, Tan Jr. B R, Poplin E, Morse M A, Beg M S. Ensituximab (E) in patients (pts) with refractory metastatic colorectal cancer (mCRC): Results of a phase 1/2 clinical trial. J Clin Oncol 35, 2017 (suppl; abstr 3081).
20. Zeligs K, Arlen P M, Tsang K, Hernandez L, Fantini M, Annunziata C M. Abstract 3025: Preclinical characterization of a novel monoclonal antibody targeting a neoantigen expressed in ovarian and GI malignancies. Cancer Res Jul. 1, 2017 (77) (13 Supplement) 3025.
21. Seidel U J, Schlegel P, Lang P. Natural killer cell mediated antibody-dependent cellular cytotoxicity in tumor immunotherapy with therapeutic antibodies. *Front Immunol.* 2013 Mar. 27; 4:76.
22. Petricevic B, Laengle J, Singer J, Sachet M, Fazekas J, Steger G, Bartsch R, Jensen-Jarolim E, Bergmann M. Trastuzumab mediates antibody-dependent cell-mediated cytotoxicity and phagocytosis to the same extent in both adjuvant and metastatic HER2/neu breast cancer patients. *J Transl Med.* 2013 Dec. 12; 11:307.
23. Dall'Ozzo S, Tartas S, Paintaud G, Cartron G, Colombat P, Bardos P, Watier H, Thibault G. Rituximab-dependent cytotoxicity by natural killer cells: influence of FCGR3A polymorphism on the concentration-effect relationship. *Cancer Res.* 2004 Jul. 1; 64(13):4664-9.
24. Levy E M, Sycz G, Arriaga J M, Barrio M M, von Euw E M, Morales S B, Gonzalez M, Mordoh J, Bianchini M. Cetuximab-mediated cellular cytotoxicity is inhibited by HLA-E membrane expression in colon cancer cells. Innate Immun. 2009 April; 15(2):91-100.
25. Kawaguchi Y, Kono K, Mimura K, Sugai H, Akaike H, Fujii H. Cetuximab induce antibody-dependent cellular cytotoxicity against EGFR-expressing esophageal squamous cell carcinoma. *Int J Cancer.* 2007 Feb. 15; 120(4):781-7.
26. López-Albaitero A, Lee S C, Morgan S, Grandis J R, Gooding W E, Ferrone S, Ferris R L. Role of polymorphic Fc gamma receptor IIIa and EGFR expression level in cetuximab mediated, NK cell dependent in vitro cytotoxicity of head and neck squamous cell carcinoma cells. *Cancer Immunol Immunother.* 2009 November; 58 (11): 1853-64. doi: 10.1007/s00262-009-0697-4.
27. Boyerinas B, Jochems C, Fantini M, Heery C R, Gulley J L, Tsang K Y, Schlom J. Antibody-Dependent Cellular Cytotoxicity Activity of a Novel Anti-PD-L1 Antibody Avelumab (MSB0010718C) on Human Tumor Cells. Cancer Immunol Res. 2015 October; 3(10):1148-57.
28. Meyer 5, Leusen J H, Boross P. Regulation of complement and modulation of its activity in monoclonal antibody therapy of cancer. MAbs. 2014; 6(5):1133-44.
29. Strome S E, Sausville E A, Mann D. A mechanistic perspective of monoclonal antibodies in cancer therapy beyond target-related effects. Oncologist. 2007 September; 12(9):1084-95.
30. Hayes J, Frostell A, Karlsson R, Müller S, Millan-Martin S, Pauers M, Reuss F, Cosgrave E, Anneren C, Davey G P, Rudd P M. Identification of Fc gamma receptor glycoforms that produce differential binding kinetics for rituximab. Mol Cell Proteomics. 2017 Jun. 2. pii: mcp.M117.066944. doi: 10.1074/mcp.M117.066944. [Epub ahead of print]
31. Koene H R, Kleijer M, Algra J, Roos D, von dem Borne A E, de Haas M. Fc gammaRIIIa-158V/F polymorphism influences the binding of IgG by natural killer cell Fc gammaRIIIa, independently of the Fc gammaRIIIa-48L/R/H phenotype. Blood. 1997 Aug. 1; 90(3):1109-14. PubMed PMID: 9242542.
32. Wu J, Edberg J C, Redecha P B, Bansal V, Guyre P M, Coleman K, Salmon J E, Kimberly R P. A novel polymorphism of FcgammaRIIIa (CD16) alters receptor function and predisposes to autoimmune disease. J Clin Invest. 1997 Sep. 1; 100(5):1059-70. PubMed PMID: 9276722
33. Musolino A, Naldi N, Bortesi B, Pezzuolo D, Capelletti M, Missale G, Laccabue D, Zerbini A, Camisa R, Bisagni G, Neri $T_M$, Ardizzoni A. Immunoglobulin G fragment C receptor polymorphisms and clinical efficacy of trastuzumab-based therapy in patients with HER-2/neu-positive metastatic breast cancer. J Clin Oncol. 2008 Apr. 10; 26(10:1789-96.
34. Hank J A, Robinson R R, Surfus J, Mueller B M, Reisfeld R A, Cheung N K, Sondel P M. Augmentation of antibody dependent cell mediated cytotoxicity following in vivo therapy with recombinant interleukin 2. Cancer Res. 1990 Sep. 1; 50(17):5234-9.
35. Watanabe M, Kono K, Kawaguchi Y, Mizukami Y, Mimura K, Maruyama T, Fujii H. Interleukin-21 can efficiently restore impaired antibody-dependent cell-mediated cytotoxicity in patients with oesophageal squamous cell carcinoma. Br J Cancer. 2010 Feb. 2; 102(3): 520-9.
36. Han K P, Zhu X, Liu B, Jeng E, Kong L, Yovandich J L, Vyas V V, Marcus W D, Chavaillaz P A, Romero C A, Rhode P R, Wong H C. IL-15:IL-15 receptor alpha superagonist complex: high-level co-expression in recombinant mammalian cells, purification and characterization. Cytokine. 2011 December; 56(3):804-10.
37. Gomes-Giacoia E, Miyake M, Goodison S, Sriharan A, Zhang G, You L, Egan J O, Rhode P R, Parker A S, Chai K X, Wong H C, Rosser C J. Intravesical ALT-803 and BCG treatment reduces tumor burden in a carcinogen induced bladder cancer rat model; a role for cytokine production and NK cell expansion. PLoS One. 2014 Jun. 4; 9(6):e96705.
38. Mathios D, Park C K, Marcus W D, Alter S, Rhode P R, Jeng E K, Wong H C, Pardoll D M, Lim M. Therapeutic administration of IL-15 superagonist complex ALT-803 leads to long-term survival and durable antitumor immune response in a murine glioblastoma model. Int J Cancer. 2016 Jan. 1; 138(1):187-94.
39. Rhode P R, Egan J O, Xu W, Hong H, Webb G M, Chen X, Liu B, Zhu X, Wen J, You L, Kong L, Edwards A C, Han K, Shi 5, Alter 5, Sacha J B, Jeng E K, Cai W, Wong H C. Comparison of the Superagonist Complex, ALT-803, to IL15 as Cancer Immunotherapeutics in Animal Models. Cancer Immunol Res. 2016 January; 4(1):49-60.
40. Kim P S, Kwilas A R, Xu W, Alter S, Jeng E K, Wong H C, Schlom J, Hodge J W. IL-15 superagonist/IL-15RaSushi-Fc fusion complex (IL-15 SA/IL-15RaSu-Fc; ALT-803) markedly enhances specific subpopulations of NK and memory CD8+ T cells, and mediates potent anti-tumor activity against murine breast and colon carcinomas. Oncotarget. 2016 Mar. 29; 7(13):16130-45.
41. Felices M, Chu S, Kodal B, Bendzick L, Ryan C, Lenvik A J, Boylan K L M, Wong H C, Skubitz A P N, Miller J S, Geller M A. IL-15 super-agonist (ALT-803) enhances natural killer (NK) cell function against ovarian cancer. Gynecol Oncol. 2017 June; 145(3):453-461.
42. Rosario M, Liu B, Kong L, Collins L I, Schneider S E, Chen X, Han K, Jeng E K, Rhode P R, Leong J W, Schappe T, Jewell B A, Keppel C R, Shah K, Hess B, Romee R, Piwnica-Worms D R, Cashen A F, Bartlett N L, Wong H C, Fehniger T A. The IL-15-Based ALT-803 Complex Enhances FcγRIIIa-Triggered NK Cell Responses and In Vivo Clearance of B Cell Lymphomas. Clin Cancer Res. 2016 Feb. 1; 22(3):596-608.
43. Seya T, Matsumoto M, Hara T, Hatanaka M, Masaoka T, Akedo H. Distribution of C3-step regulatory proteins of the complement system, CD35 (CR1), CD46 (MCP), and CD55 (DAF), in hematological malignancies. Leuk Lymphoma. 1994 February; 12(5-6):395-400.
44. Niehans G A, Cherwitz D L, Staley N A, Knapp D J, Dalmasso A P. Human carcinomas variably express the complement inhibitory proteins CD46 (membrane cofactor protein), CD55 (decay-accelerating factor), and CD59 (protectin). Am J Pathol. 1996 July; 149(1):129-42.
45. Donin N, Jurianz K, Ziporen L, Schultz S, Kirschfink M, Fishelson Z. Complement resistance of human carcinoma cells depends on membrane regulatory proteins, protein kinases and sialic acid. Clin Exp Immunol. 2003 February; 131(2):254-63.
46. Hsu Y F, Ajona D, Corrales L, Lopez-Picazo J M, Gurpide A, Montuenga L M, Pio R. Complement activation mediates cetuximab inhibition of non-small cell lung cancer tumor growth in vivo. Mol Cancer. 2010 Jun. 7; 9:139.
47. Konishi E, Kitai Y, Kondo T. Utilization of complement-dependent cytotoxicity to measure low levels of antibodies: application to nonstructural protein 1 in a model of Japanese encephalitis virus. Clin Vaccine Immunol. 2008 January; 15(1):88-94.
48. David J M, Dominguez C, McCampbell K K, Gulley J L, Schlom J, Palena C. A novel bifunctional anti-PD-L1/TGF-β☐ Trap fusion protein (M7824) efficiently reverts mesenchymalization of human lung cancer cells. OncoImmunology. 2017 Jul. 13; 6(10):e1349589.
49. Beyer M et al. Blood 2005, 106, 2018.
50. Motta M et al. Leukemia 2005, 19:1788.
51. Yang Z Z et al. Blood, 2006, 107:3639.
52. Woo et al. Cancer Res 2001, 61:4766.
53. Javia et al. J Immunother. 2003, 26:85.
54. Sasada et al. Cancer, 2003:98:1089.
55. Curiel J T et al. Nat Med 2004, 10:942.
56. Schaefer et al. Br. J. Cancer 2005, 92:913.
57. Ormandy L A et al. Cancer Res, 2005:2457.
58. Liyanage U Y et al. J Immunol, 2002, 169:2756.
59. Delong P, et al. Cancer Bio Ther 2006, 4:342.
60. Dannull J et al. J Clin Invest, 2005, 115: 3623.
61. Vergati M et al. Cancer Immunol Immunother. 2011, 60:197.
62. Miller A M, et al. J Immunol 2066, 177:7398.
63. Mukhetji B. J Exp Med. 1989, 169:1961.
64. Chakraborty N G et al. J Immunol 1990, 145:2359.
65. Barnett B et al. Am J Reprod Immunol 2005, 54:369.
66. Antony P A, et al. J Immunother 2002, 25:202.

The invention claimed is:

1. A method of treating cancer in a patient in need thereof, comprising administering an effective amount of an antibody comprising a VH and VL polypeptide comprising the same CDR sequences respectively contained in SEQ ID NO: 28 and SEQ ID NO: 29, wherein said patient comprises a cancer which is CEACAM5 and CEACAM6 negative, wherein said method:
   (a) kills Treg cells in said patient or decreases Treg cell infiltration into said CEACAM5 and CEACAM6 negative cancer in said patient; thereby
   (b) potentiating anti-cancer immune responses against said CEACAM5 and CEACAM6 negative cancer in said patient; and
   (c) reducing the number of CEACAM5 and CEACAM6 negative cancer cells or the growth or proliferation rate of said CEACAM5 and CEACAM6 negative cancer in the patient wherein the method further comprising, prior to or at the time of said administering, determining that said cancer is CEACAM5 and CEACAM6 negative and/or does not specifically bind to the antibody.

2. The method of claim 1, further comprising administering a cancer vaccine to said patient.

3. The method of claim 1, further comprising administering another therapeutic agent to said patient.

4. The method of claim 3, wherein said other agent is selected from (a) microtubule inhibitors, topoisomerase inhibitors, platins, alkylating agents, and anti-metabolites; (b) MK-2206, ON 013105, RTA 402, B12536, Sorafenib, ISIS-STAT3Rx, a microtubule inhibitor, a topoisomerase inhibitor, a platin, an alkylating agent, an anti-metabolite, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and vinorelbine; (c) 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues; (d) a PD-1 inhibitor or anti-PD-1 antibody; or (e) a CTLA-4 inhibitor or anti-CTLA-4 antibody.

5. The method of claim 1, wherein said antibody is coupled to a cytotoxic moiety.

6. The method of claim 1, wherein said antibody comprises:
   (i) a variable heavy chain sequence having at least 90% identity to SEQ ID NO: 38;
   (ii) a variable light chain sequence having at least 90% identity to SEQ ID NO: 39;
   (iii) a variable heavy chain sequence having at least 90% identity to SEQ ID NO: 38 and a variable light chain sequence having at least 90% identity to SEQ ID NO: 39; or
   (iv) a heavy chain sequence having at least 90% identity to amino acids 20-470 of SEQ ID NO: 28 and a light chain sequence having at least 90% identity to amino acids 20-233 of SEQ ID NO: 29.

7. The method of claim 1, wherein said antibody comprises a human IgG1 constant domain.

8. The method of claim 1, wherein said antibody is humanized.

9. The method of claim 1, wherein said antibody is conjugated to another moiety.

10. The method of claim 1, wherein said antibody is conjugated to another cytotoxic moiety, label, radioactive moiety, or affinity tag.

11. The method of claim 1, wherein said cancer which is CEACAM5 and CEACAM6 negative is selected from hematologic malignancies, lung cancers, melanoma, gastrointestinal malignancies, ovarian cancer, squamous cell carcinoma of the head and neck, hepatocellular carcinoma, breast cancer, pancreatic cancer, mesothelioma, metastatic renal cell carcinoma, and prostatic cancer.

12. The method of claim 1, wherein the treated cancer is not colon cancer, breast cancer, prostate cancer or lymphoma.

* * * * *